US00PP11083P

United States Patent [19]

Nicholls

[11] Patent Number: Plant 11,083

[45] Date of Patent: Oct. 12, 1999

[54] HONEYSUCKLE PLANT NAMED 'MANDARIN'

[75] Inventor: Kevin W. Nicholls, St. John's, Canada

[73] Assignee: The University of British Columbia Botanical Garden, Vancouver, Canada

[21] Appl. No.: 08/985,547

[22] Filed: Dec. 5, 1997

[51] Int. Cl.[6] ..... A01H 5/00

[52] U.S. Cl. ..... Plt./226

[58] Field of Search ..... Plt./54.1, 226

*Primary Examiner*—Howard J. Locker
*Assistant Examiner*—Anne Marie Grünberg
*Attorney, Agent, or Firm*—Burns, Doane, Swecker & Mathis, L.L.P.

[57] ABSTRACT

A new and distinct Lonicera hybrid (Honeysuckle) plant is provided that forms attractive, extremely large tubular-shaped flowers. Such flowers are a dark reddish-orange on the outside and a paler reddish-orange on the inside. The foliage coloration contrasts nicely with the flower coloration and initially is brownish and with maturity becomes glossy deep green. The growth habit is vigorous thereby making possible the formation of a unique colorful screening vine within a relatively short period of time. The new cultivar grows particularly well on a trellis or fence.

2 Drawing Sheets

SUMMARY OF THE INVENTION

The new Lonicera hybrid plant of the present invention is a member of the Caprifoliaceae family and was created by artificial pollination wherein two parents were crossed which previously had been studied in the hope that they would contribute the desired characteristics. The initial cross was conducted during 1989 at the University of British Columbia Botanical Garden located at Vancouver, British Columbia, Canada. The female parent (i.e., the seed parent) was *Lonicera tragophylla* (non-patented in the United States) and the male parent (i.e., the pollen parent) was *L.×brownii* 'Dropmore Scarlet' (non-patented in the United States). The parentage of the new cultivar can be summarized as follows:

(*Lonicera tragophylla×L.×brownii* 'Dropmore Scarlet').

The seeds resulting from the above pollination were sown and plants were obtained which were found to be physically and biologically different from each other. The plant which forms the subject matter of the present application first flowered during 1991. Selective study of the offspring resulting from the above-identified cross has resulted in the identification of a single plant of the new cultivar.

It was found that the new Lonicera hybrid plant of the present invention possesses the following combination of characteristics:

(a) forms attractive very large tubular-shaped flowers that are dark reddish-orange on the outside and a paler yellow-orange on the inside,
(b) exhibits a vigorous growth habit,
(c) forms leaves that initially are brownish in coloration and with maturity become glossy deep green, and
(d) has the ability to grow well on a trellis or fence.

The new variety well meets the needs of the horticultural industry. It is particularly well-suited for use as attractive ornamentation in the landscape where it offers an array of color during much of the growing season. The new cultivar grows well when supported such as on a trellis, fence, or when cascading over a wall. It can serve as an extremely rapidly growing woody screening vine to provide summer privacy. It also provides good attraction for hummingbirds.

The new cultivar readily can be shipped and marketed while growing in one, two or five gallon pots.

The new cultivar has been found to readily undergo asexual reproduction through the use of cuttings. It has been found that superior results are achieved when soft/semi-ripe node cuttings having a length of approximately 4 cm. are obtained during July–August from stock plants that are grown outdoors. For instance, such cuttings can be given a 1 cm. slice wound and a 50 percent reduction in leaf area, soaked for approximately one minute in a weak disinfectant (e.g., Physan disinfectant), dipped in a rooting powder (e.g., Stimroot No. 3 rooting powder), directly stuck in 2¼ inch pots of 50/50 peat/Perlite planting medium, and provided under mist with a bottom heat of 20° C. Rooting commonly takes 4 to 6 weeks under such conditions. Cuttings taken later in the year sometimes result in overwintering problems at Vancouver, British Columbia, Canada.

The new cultivar of the present invention has been accorded Accession No. 32362-51-89 of the University of British Columbia Botanical Garden, and has been named the 'Mandarin' cultivar. The new cultivar also has been registered with the Canadian Ornamental Plant Foundation.

BRIEF DESCRIPTION OF THE PHOTOGRAPHS

The accompanying photographs show, as nearly true as it is reasonably possible to make the same in color illustrations of this character, typical mature specimens of plants of the new cultivar. The illustrated plants were grown at Vancouver, British Columbia, Canada.

DETAILED DESCRIPTION

The chart used in the identification of the colors is that of The Royal Horticultural Society (R.H.S. Colour Chart). Color terminology also is provided in common terms that are to be accorded their usual dictionary significance. The description is based upon the observation of mature plants of the new cultivar while growing in the landscape at Victoria, British Columbia, Canada. The illustrated plants had been asexually reproduced through the use of cuttings.

Family: Caprifoliaceae.
Botanical name: Lonicera hybrid.
Common name: 'Mandarin' Honeysuckle Vine.
Parentage: *Lonicera tragophylla*×*L.*×*brownii* 'Dropmore Scarlet'.

*Growth habit.*—Vigorous deciduous woody vine that can assume a length of approximately 6 m. or more at maturity. A growth length of approximately 2 m. may form during a single growing season.

Figure 1:
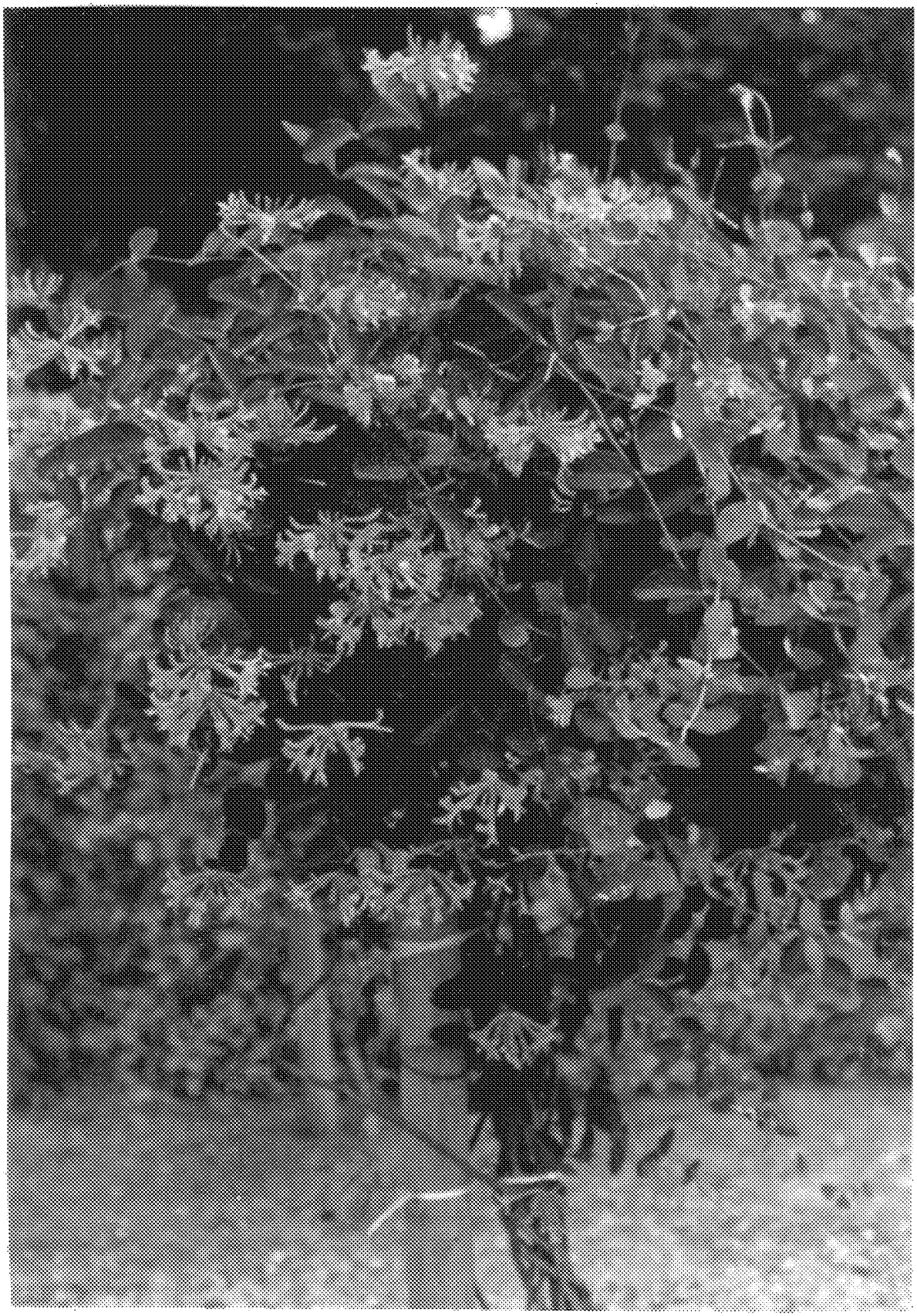
FIG. 1 illustrates an overall view of a supported plant while flowering during late springtime.
Figure 2:
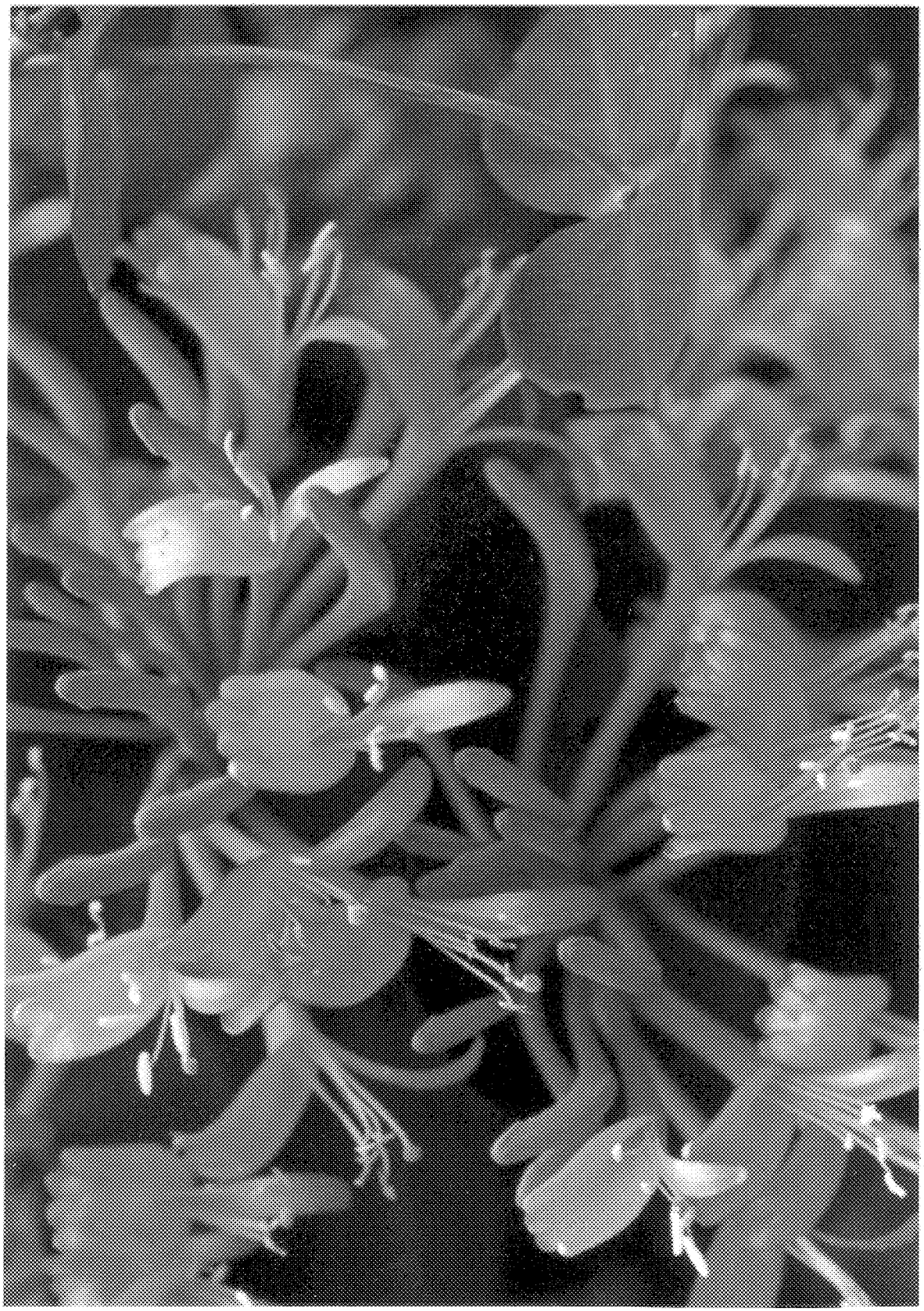
FIG. 2 illustrates a closer view of the flowers in various stages of opening during late springtime as well as leaflets that are borne in a sessile pair and a stem.

*Foliage.*—Leaves on non-flowering shoots. Obovate, when young purplish-brown or coppery-brown above and turning to glossy dark green on the upper surface (near Yellow-Green Group 147A) and a lighter green on the under surface (near Greyed-Green Group 191A) at maturity (as illustrated), glabrous throughout, glaucous beneath, mostly borne in sessile pairs or short petiolate, commonly approximately 3 to 4 cm. in length and approximately 2 to 3 cm. in width with entire margins. Leaves on flowering shoots. Oblong or ovate, dark green on the upper surface (near Yellow-Green Group 147A) and a lighter green on the under surface (near Greyed-Green Group 191A) often with a red midrib when mature (near Greyed-Red Group 178A on the upper surface especially towards the base and near Greyed-Yellow Group 160B on the under surface) especially when in full sun, glabrous, glaucose beneath, commonly borne in 3 to 5 pairs wherein lower leaves commonly are sessile or short-petiolate having a length of approximately 5 to 10 cm. and a width of approximately 3 to 6 cm., and the upper leaves are commonly orbicular perfoliate forming an upturned cup with entire margins. Stems: Young stems are dark purplish-brown (as illustrated in FIG. 2), changing to coppery coloration (as illustrated in FIG. 1).

*Inflorescence.*—Time. Primarily during May and June and then periodically throughout the summer until fall. Configuration. As long slender floral tubes of approximately 4 to 5 cm. or more in length, commonly possess five petals with four petals being fused for most of their lengths and curved upward, and the fifth petal being substantially free and curved downward. Bearing. Commonly in three or four whorls positioned close to each other thereby forming a head-like cluster of approximately 15 to 30 flowers that usually are all curved to one side. Coloration. Dark reddish-orange, Orange-Red Group 34B, on the outside and a paler yellow-orange, Yellow-Orange Group 23B, on the inside. Reproductive Organs. When fully open five stamens and a style commonly extend beyond the tube for a substantial distance (as illustrated in FIG. 2). Overall Flower Appearance. Intense orange or bright pumpkin coloration when seen from a distance which influenced the selection of the 'Mandarin' cultivar name. The flower coloration contrasts attractively with the coloration of the leaves and stems. Fragrance. The flowers tend to exhibit a diurnal scent-releasing rhythm. More specifically, the flowers commonly are fragrant during the morning hours and tend to approach a scentless state by midday. Fruit formation. Occasionally small non-maturing green fruits form and promptly dehisce. Mature fruits have not been observed to date. For all practical purposes fruit is not produced.

*Hardiness.*—Testing to date within North America indicates a hardiness rating of at least USDA Zone 4 (Canadian Zone 4). Test plants have survived for several winters at Morden, Manitoba, Canada having USDA Zone 3 (Canadian Zone 3) with little winter damage.

*Soil requirements.*—Average, well-drained to moist soils. Is tolerant of neutral to acid soils.

*Exposure.*—Partial shade to full sun, but needs a somewhat cool root area.

*Pruning.*—Can be pruned in winter to maintain a desired length.

*Disease resistance.*—Generally no disease problem has been observed to date with the exception of an occasional isolated mildew attack.

*Heat tolerance.*—Good.

I claim:

1. A new and distinct Lonicera hybrid cultivar which exhibits the following combination of characteristics:

(a) forms attractive very large tubular-shaped flowers that are dark reddish-orange on the outside and a paler yellow-orange on the inside,
(b) exhibits a vigorous growth habit,
(c) forms leaves that initially are brownish in coloration and with maturity become glossy deep green, and
(d) has the ability to grow well on a trellis or fence;

substantially as illustrated and described.

* * * * *